(12) United States Patent
Perlin

(10) Patent No.: US 7,177,026 B2
(45) Date of Patent: Feb. 13, 2007

(54) BRDF ANALYZER

(75) Inventor: Kenneth Perlin, New York, NY (US)

(73) Assignee: New York University, New York, NY (US)

( * ) Notice: Subject to any disclaimer, the term of this patent is extended or adjusted under 35 U.S.C. 154(b) by 95 days.

(21) Appl. No.: 10/665,804

(22) Filed: Sep. 19, 2003

(65) Prior Publication Data

US 2004/0061784 A1 Apr. 1, 2004

Related U.S. Application Data

(63) Continuation-in-part of application No. 10/620,920, filed on Jul. 16, 2003.

(60) Provisional application No. 60/413,533, filed on Sep. 25, 2002, provisional application No. 60/396,697, filed on Jul. 17, 2002.

(51) Int. Cl.
*G01N 21/47* (2006.01)
*G01N 21/55* (2006.01)

(52) U.S. Cl. ........................................ 356/446; 356/445

(58) Field of Classification Search ......... 356/445–446
See application file for complete search history.

(56) References Cited

U.S. PATENT DOCUMENTS 5,637,873 A * 6/1997 Davis et al. ............ 250/339.11
6,873,417 B2 * 3/2005 Bahatt et al. ................ 356/445

* cited by examiner

*Primary Examiner*—Gregory J. Toatley, Jr.
*Assistant Examiner*—Amanda Merlino
(74) *Attorney, Agent, or Firm*—Ansel M. Schwartz

(57) ABSTRACT

An apparatus for determining a bidirectional reflectance distribution function of a subject. The apparatus includes a light source for producing light. The apparatus includes sensing means for sensing the light. The apparatus includes means for focusing the light between the light source and the sensing means and the subject. The apparatus includes a computer connected to the sensing means for measuring the bidirectional reflectance distribution function of the subject from the light sensed by the sensing means. The apparatus can include only one CCD camera for sensing the light. The apparatus can include means for taking sub-measurements of the subject with light from the light source without any physical movement between sub-measurements. A method for determining a bidirectional reflectance distribution function of a subject.

34 Claims, 2 Drawing Sheets

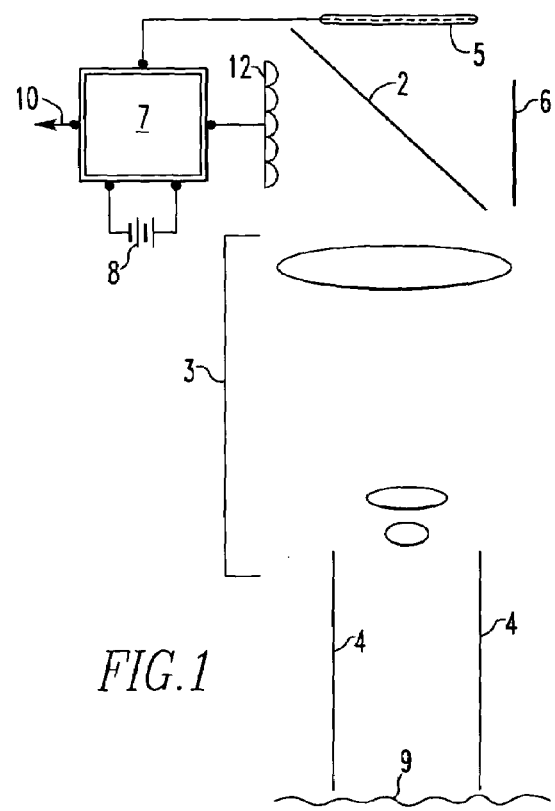
FIG.1
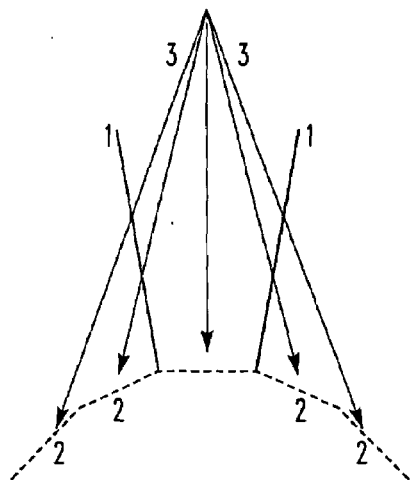
FIG.2
FIG.2B

US 7,177,026 B2

BRDF ANALYZER

This application claims the benefit of U.S. Provisional Application Nos.: 60/413,533 Sep. 25, 2002.

This application is a continuation-in-part of copending application application Ser. No. 10/620,920 filed on Jul. 16, 2003.

The nonprovisional application designated above, namely application Ser. No. 10/620,920, filed Jul. 16, 2003, claims the benefit of U.S. Provisional Application Nos.: 60/396,697 Jul. 17, 2002.

FIELD OF THE INVENTION

The present invention is related to determining a bidirectional reflectance distribution function of a subject. More specifically, the present invention is related to determining a bidirectional reflectance distribution function of a subject with a hollow tube lined with mirrors through which light from light source passes, reflecting zero or more times off of the mirrors.

BACKGROUND OF THE INVENTION

The way that any point on a surface interacts with light can be described by its Bidirectional Reflectance Distribution Function, or BDRF. This function is a mapping from the two dimensions of incoming light direction to the two dimensions of outgoing light direction, or a mapping from (u,v) to (u',v'). In order to create visually realistic computer graphic simulations of complex real-world surfaces, such as wood or woven fabric or human skin, it is useful to measure the actual BRDF of such surfaces. For example, once the BRDF of small patches of skin on a human face have been measured, then the surface of an entire new face can be synthesized by seamlessly patching together such samples. The visually realistic synthesis of large areas of textured surfaces from small example patches is well known in the literature [A. Efros and W. Freeman. Image Quilting for Texture Synthesis and Transfer. *Proceedings of SIGGRAPH* '01, Los Angeles, Calif., August, 2001, incorporated by reference herein].

One bottleneck to this process is the need to measure the BRDF of real-world samples. Current techniques to do this are highly invasive, in that they require the sample to be placed in a specially lit environment [S. Marschner, S. Westin, E. Lafortune, K. Torrance, and D. Greenberg. Image-based BRDF Measurement Including Human Skin. In 10*th Eurographics Workshop on Rendering,* pages 131–144, June 1999, incorporated by reference herein]. For some surfaces, such as living human skin, which cannot be placed by itself in an isolated measuring chamber, this is a difficult, tedious and expensive process.

The following is a description of a device to quickly and accurately measure the BDRF of a sample region of a surface in situ. The device can be made small and portable, requires no moving parts, and can be used in any lighting situation.

The new technique requires no physical movement between sub-measurements, thereby guaranteeing that all sub-measurements will be perfectly registered with one another. This property allows an improvement in accuracy in comparison with previous methods for measuring BRDF that require physical movement between sub-measurements.

Also, the new technique requires only a single CCD camera or equivalent image capture device. This property allows the device to be fabricated at a low cost in comparison with previous methods that require multiple CCD cameras or equivalent image capture devices.

All of these qualities make the new method a valuable measurement tool for use in situations for which current techniques are too bulky or unwieldy. For example, during a motion picture production, a computer graphics special effects expert could use a device employing the new method to measure the response to light of the skin of various parts of an actor's face, or the fabric of a costume, or a prop or other part of the set. With this information in hand, then through the use of currently known techniques in computer graphics synthesis [P. Hendrik, J. Lansch, M. Goesele, W. Heidrich and H. Seidel. Image-Based Reconstruction of Spatially Varying Materials. In *Twelfth Eurographics Rendering Workshop* 2001, pages 104–115, Eurographics, June 2001, incorporated by reference herein], the appearance of these items can then be duplicated digitally with highly convincing realism and fidelity.

SUMMARY OF THE INVENTION

The present invention pertains to an apparatus for determining a bidirectional reflectance distribution function of a subject. The apparatus comprising a light source for producing light. The apparatus comprising sensing means for sensing the light. The apparatus comprising means for focusing the light between the light source and the sensing means and the subject. The apparatus comprising a computer connected to the sensing means for measuring the bidirectional reflectance distribution function of the subject from the light sensed by the sensing means.

The present invention pertains to a method for determining a bidirectional reflectance distribution function of a subject. The method comprises the steps of placing an optically hollow structure against the subject. There is the step of producing light. There is the step of reflecting the light at various angles from the subject through the hollow structure. There is the step of measuring the bidirectional reflectance distribution function from the reflected light.

BRIEF DESCRIPTION OF THE DRAWINGS

In the accompanying drawings, the preferred embodiment of the invention and preferred methods of practicing the invention are illustrated in which:

FIG. 1 is a schematic representation of a preferred embodiment of the present invention.

FIG. 2*a* shows the sequence of mirror reflects corresponding to each sub-square of the captured image.

FIG. 2*b* shows a hollow tube with slanted walls.

FIG. 4 is a schematic representation of the present invention.

DETAILED DESCRIPTION

Figure 3:
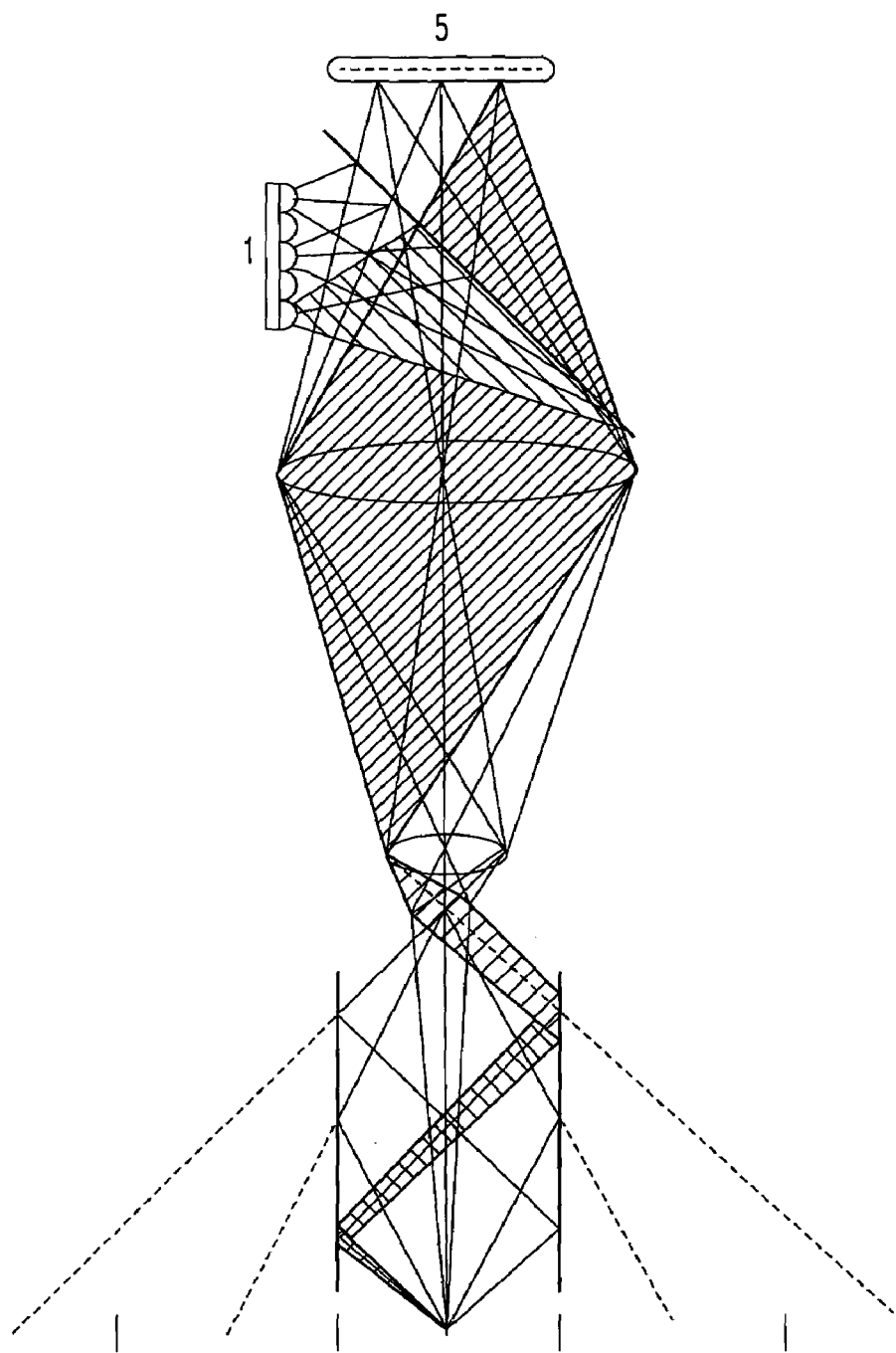
FIG. 3 shows a path of light through the apparatus.

Referring now to the drawings wherein like reference numerals refer to similar or identical parts throughout the several views, and more specifically to FIGS. 1 and 4 thereof, there is shown an apparatus 10 for determining a bidirectional reflectance distribution function of a subject. The apparatus 10 comprises a light source 12 for producing light. The apparatus 10 comprises sensing means 14 for sensing the light. The apparatus 10 comprises means 16 for focusing the light between the light source 12 and the sensing means 14 and the subject. The apparatus 10 comprises a computer 7 connected to the sensing means 14 for measuring the bidirectional reflectance distribution function of the subject from the light sensed by the sensing means 14.

Preferably, the sensing means 14 includes a light absorbing wall 6 which absorbs unwanted light from the light source 12. The focusing means 16 preferably includes a hollow tube 4 lined with mirrors 24 through which light from light source 12 passes, reflecting zero or more times off of the mirrors 24. Preferably, the sensing means 14 includes an image sensing device 5 for sensing light of the subject that has passed through the focusing means 16. The focusing means 16 preferably includes a half silvered mirror 2 which directs light from the light source 12 to the hollow tube 4 and light from the hollow tube 4 to the image sensing device 5.

Preferably, the focusing means 16 includes a magnifying lens system 3 for directing the light to the hollow tube 4. The light source 12 preferably includes an array of LEDs. Preferably, the computer 7 causes the lights in the LED array 1 to turn on in sequence, with light from each LED taking a sub-measurement of the bidirectional reflectance distribution function. The imaging sensing device preferably includes a CCD camera 34. Preferably, the tube 4 has a square profile.

The hollow tube 4 can have slanted walls, with a profile that is larger at its top end and smaller at its bottom end, as shown in FIG. 2a.

The present invention pertains to a method for determining a bidirectional reflectance distribution function of a subject. The method comprises the steps of placing an optically hollow structure against the subject. There is the step of producing light. There is the step of reflecting the light at various angles from the subject through the hollow structure. There is the step of measuring the bidirectional reflectance distribution function from the reflected light.

Preferably, the producing step includes the step of triggering light sequentially from each LED from an array of LEDs, the computer 7 in communication with the LEDs. The reflecting step preferably includes the step reflecting light off of mirrors 24 in the hollow structure. Preferably, the reflecting step includes the step reflecting the light from a half silvered mirror to the hollow structure.

The reflecting step preferably includes the step of imaging light from the LEDs with a magnifying lens system 3 onto the surface through the hollow structure. Preferably, the reflecting step includes the step of reflecting light off of the first wall of a hollow structure. The reflecting step preferably includes the steps of reflecting light off a right wall of the hollow structure, reflecting the light off a left wall of the structure, striking the surface with a light, reflecting light off the left wall, reflecting the light off the right wall, passing the light through the lens, traveling the light through the half-silvered mirror 2, and impinging the light on the CCD camera 34.

The present invention pertains to an apparatus 10 for determining a bidirectional reflectance distribution function of a subject. The apparatus 10 comprising a light source 12 for producing light. The apparatus 10 comprising only one CCD camera 34 for sensing the light. The apparatus 10 comprising means for focusing the light between the light source 12 and the sensing means 14 and the subject. The apparatus 10 comprising a computer 7 connected to the CCD camera 34 for measuring the bidirectional reflectance distribution function of the subject from the light sensed by the sensing means 14.

The present invention pertains to an apparatus 10 for determining a bidirectional reflectance distribution function of a subject. The apparatus 10 comprising a light source 12 for producing light. The apparatus 10 comprising means 36 for taking sub-measurements of the subject with light from the light source 12 without any physical movement between sub-measurements. The apparatus 10 comprising a computer 7 connected to the taking means for measuring the bidirectional reflectance distribution function of the subject from the light sensed by the taking means.

In the operation of the invention, FIG. 1 shows the components of the device.

1. Structured light source 12, such as an array of LEDs
2. Half-silvered mirror 2 or optical equivalent
3. Magnifying lens system 3
4. Optically hollow square-profiled tube 4, internally lined with four front-surface mirrors 24: a left mirror, a right mirror, a front mirror and a rear mirror
5. Image sensing/capture array, such as a CCD device
6. Light absorbing wall 6
7. Computer 7
8. Electric power source
9. The surface to be measured
10. Image output port or storage device The device is placed flush against the surface to be measured, with the open end of the optically hollow square-profiled tube 4 placed against the surface sample. The device is held in that position for a short period of time ranging from about half a second to several seconds. The computer 7 makes available the resulting measured BRDF in the form of a sequence of images of the same small region of the surface, as lit from a variety of angular directions and, for each such angular lighting direction, as viewed from a variety of angular directions. This information can then be used by image synthesis algorithms.

When the optically hollow square-profiled tube 4 is held against the surface sample 9, the user of the device triggers the computer 7 to cause the lights in the LED array 1 to turn on one by one, in sequence, with light from each LED taking a sub-measurement for the measurement of the BRDF. Light from 1 reflects off the half-silvered mirror 2, and is imaged by the magnifying lens system 3 onto the surface 9, after zero or more reflections off each of the front-surface mirrors 24 that line the four walls of the optically hollow square-profiled tube 4.

Purpose of the light absorbing wall 6: The light absorbing wall 6 absorbs unwanted stray light from the LED array 1 which might otherwise pass through the half-silvered mirror 2 and then reflect up onto the image sensing/capture array 5.

Geometry of the optically hollow tube 4: The square-profiled optically hollow tube 4 forms a rectilinear kaleidoscope, of length such that the sample surface 9 abutting the tube's bottom edge is focused by the magnifying lens array on the image sensor 5. Alternatively, the optically hollow tube 4 can have a triangular profile, or an oblong rectangular profile, since these geometries also form a kaleidoscope. If a person were to visually examine the image of the small surface sample by peering down into this tube 4, that person would observe a two dimensional mosaic of square images of the sample. Each image in this array appears to the observer to be offset by a discrete amount in the front/rear direction, as well as in the left/right direction.

This property is exploited to enable each LED in the LED array 1 to illuminate the sample 9 from many different angular directions. This same property is also exploited to enable the image sensing device 5 to view the sample 9 from many different angular directions.

The walls of the hollow tube may be slanted, so that the profile of the tube is larger at its top end and smaller at its bottom end. This will have the effect that the sequence of reflected images seen through the tube appear to bend away from the observer. This geometry increases the angular difference between successive reflections, both of light arriving at the surface from different LEDs, and of light going out from the surface to different portions of the image sensing device.

FIG. 2b illustrates this. The slanted mirrored walls (1) result in the successive reflections of the surface (2) to appear to be successively more slanted. This results in the light rays (3) from or to the optical system to encounter these reflected surface views at progressively more slanted angles.

The use of this kaleidoscopic element allows sub-measurements to be made without the need for any physical movements between sub-measurements. This property allows the device to function with only one CCD camera 34 or equivalent image capture device.

Each LED in 1 is positioned so that light from that LED will reach the surface sample after a particular sequence of reflections off the set of front-surface mirrors 24. For example, the LED in the middle will be focused by the lens system 3 directly onto the surface sample 9, without reaching any of the tube 4 walls. The LED just above this one will reflect once off the left mirror. The LED above that one will reflect once off the left mirror, and then once off the right mirror, before reaching the sample.

Similarly, the LED just to the left of the center LED will reflect once off the rear mirror. The LED to the left of that one will reflect once off the rear mirror, and then once off the front mirror, before reaching the sample.

Measurement the surface BRDF proceeds by taking a sequence of successive sub-measurements, one after the other. During each sub-measurement, exactly one of the LEDs is lit, and the others are kept dark. Because each LED corresponds to a unique sequence of reflections of light off of the tube 4 walls, that LED will illuminate the surface sample 9 from a unique sub-range of incoming light directions. A complete measurement consists of successive illumination of the surface sample by each of the LEDs in turn. The number of images captured by the image capture device during a complete measurement will equal the number of LEDs in the LED array 1.

Placement of the LED array 1 and image array: The LED array 1 and image sensing/capture array 5 are placed at the same distance from the half-silvered mirror 2. This ensures that the magnifying lens system 3 will focus light from the LED array 1 onto the surface 9, and will also focus the returning light from the surface onto the image sensing/capture array.

The light from any given LED is scattered back upward by each point of the sample into various directions. Each square sub-region of the image capture device receives light focused from the surface by the lens system 3, after that light has reflected in a particular sequence off the left, right, front and rear mirrors that line the tube 4.

Effect of varying magnification of the magnifying lens system 3: If the magnifying lens system 3 is provided with greater magnification, then at the maximum number of reflections, the light from the LED array 1, as well as the returning light from the surface to the image sensing/capture array, will be angled more obliquely with respect to the surface normal direction, thereby allowing BRDF measurement through a greater range of directions. But as the magnification is increased, the aperture of the magnifying lens system 3 needs to be correspondingly decreased, thereby requiring correspondingly more powerful LEDS and/or longer exposure times to send the same number of photons to the image sensing/capture array.

FIG. 2 shows the sequence of mirror reflects corresponding to each sub-square of the captured image.

FIG. 3 shows the following path of light:
1. emitted from an LED,
2. reflecting off the half-silvered mirror 2,
3. passing down through the lens system 3,
4. reflecting off the right wall,
5. reflecting off the left wall,
6. striking the surface sample,
7. reflecting off the left wall,
8. reflecting off the right wall,
9. passing up through the lens system 3,
10. traveling through the half-silvered mirror 2,
11. impinging on the imaging element.

In the preferred embodiment, the image is captured by a high definition digital camera 34. Using a 1500×1500 camera, a 5×5 tiling is captured, where each tiling is 300×300 pixels. In this case, the LED array 1 consists of a 5×5 array of LEDs. Alternatively, we can use more or fewer LEDs. For example, a 7×7 tiling is captured, where each tiling is 214×214 pixels. In this case, the LED array 1 consists of a 7×7 array of LEDs.

In the preferred embodiment a collimating lens is placed in front of each LED or equivalent light source 12. The lens in front of each LED is positioned such that the LED is imaged by the lens onto the aperture of the magnifying lens system. These lenses can be inexpensive, and can be made out of an inexpensive material such as plastic, since they are required only to collimate light, not to form a high quality image. These collimating lenses increase optical efficiency of the device, because they will cause more light from each LED to pass through the magnifying lens array, and therefore to reach the surface sample. In this way, the use of collimating lenses will increase the optical efficiency of the illumination source, reduce unwanted light scatter, and reduce the required exposure time for a given power of light source.

One can capture different color characteristics in several ways. One way is to rely on the Red/Green/Blue components of a digital camera, and use white LEDs for the illumination. Another way is to use a gray-scale digital camera, and use separate Red/Green/Blue LEDs.

The sequence of captured images can be stored locally in the device, for example on a magnetic disk storage device. Alternatively the information can be directly transmitted via wire or wireless connection (such as radio frequency or line-of-sight infrared) to a computer for further processing.

The optically hollow tube 4 can be a physically hollow tube 4, with inside walls that are lined with front-surface mirrors 24. Alternatively, it can be a solid block, made out of an optically clear material such as glass, with walls that are lined with reflecting material.

Each reflection off of a front-surface mirror causes a small loss of light. A front-surface mirror typically has about 93% efficiency. This means that the total fraction of light available in any path from LED to image sub-tile is dependent upon the total number of mirror reflections $r_L$ between LED and surface, and the total number of mirror reflections $r_I$ between surface and image capture device. This fraction will be $0.93^{(r_L + r_I)}$. Because this light-loss per reflection is known, it can be compensated for accurately within the computer graphic program that analyzes the image from the CCD to reconstruct an approximation to the BRDF of the surface.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for determining one or more values of a bidirectional reflectance distribution function of a subject comprising:
   sensing means for sensing light;
   means for focusing the light between the sensing means and the subject; and
   a computer connected to the sensing means for measuring one or more values of the bidirectional reflectance distribution function of a plurality of locations of the subject simultaneously from the light sensed by the sensing means.

2. An apparatus as described in claim 1 including a light source for producing light.

3. An apparatus as described in claim 2 wherein the sensing means includes a light absorbing wall which absorbs unwanted light from the light source.

4. An apparatus as described in claim 2 wherein the light source has multiple individually addressable light elements.

5. An apparatus as described in claim 4 wherein the light source includes an array of LEDs.

6. An apparatus as described in claim 5 wherein the computer causes the lights in the LED array to turn on in sequence, with light from each LED taking a sub-measurement of the bidirectional reflectance distribution function.

7. An apparatus as described in claim 1 wherein the focusing means includes reflecting surfaces through which light from the light source passes, reflecting zero or more times off of the reflecting surfaces.

8. An apparatus as described in claim 1 wherein the sensing means includes an image sensing device for sensing light of the subject that has passed though the focusing means.

9. An apparatus as described in claim 8 wherein the reflecting surfaces are mirrors.

10. An apparatus as described in claim 9 wherein the focusing means includes a hollow tube lined with the mirrors.

11. An apparatus as described in claim 10 wherein the focusing means includes a half silvered mirror which directs light from the light source to the hollow tube and light from the hollow tube to the image sensing device.

12. An apparatus as described in claim 11 wherein the focusing means includes a magnifying lens system for directing the light to the hollow tube.

13. An apparatus as described in claim 10 wherein the hollow tube has slanted walls.

14. An apparatus as described in claim 10 wherein the tube has a profile that is larger at its top end and is smaller at the bottom end.

15. An apparatus as described in claim 8 wherein the imaging sensing device includes a CCD camera.

16. An apparatus as described in claim 15 wherein the tube has a square profile.

17. A method for determining one or more values of a bidirectional reflectance distribution function of a subject comprising the steps of:
   placing an optically hollow structure adjacent to the subject;
   producing light;
   reflecting the light at various angles from the subject through the hollow structure; and
   measuring the bidirectional reflectance distribution function of a plurality of locations of the subject simultaneously from the reflected light.

18. A method as described in claim 17 wherein the producing step includes the step of triggering light sequentially from each LED from an array of LEDs, the computer in communication with the LEDs.

19. A method as described in claim 18 wherein the reflecting step includes the step reflecting light off of mirrors in the hollow structure.

20. A method as described in claim 19 wherein the reflecting step includes the steps of reflecting light off a right wall of the hollow structure, reflecting the light off a left wall of the structure, striking the surface with a light, reflecting light off the left wall, reflecting the light off the right wall, passing the light through the lens, traveling the light through the half-silvered mirror, and impinging the light on the CCD camera.

21. A method as described in claim 20 wherein the reflecting step includes the step reflecting the light from a half silvered mirror to the hollow structure.

22. A method as described in claim 21 wherein the reflecting step includes the step of imaging light from the LEDs with a magnifying lens system onto the surface through the hollow structure.

23. A method as described in claim 22 wherein the reflecting step includes the step of reflecting light off of the first wall of a hollow structure.

24. An apparatus for determining one or more values of a bidirectional reflectance distribution function of a subject comprising:
   a light source for producing light;
   only one CCD camera for sensing the light;
   means for focusing the light between the light source and the sensing means and the subject; and
   a computer connected to the CCD camera for measuring one or more values of the bidirectional reflectance distribution function of a plurality of locations of the subject simultaneously from the light sensed by the sensing means.

25. An apparatus as described in claim 24 wherein the light source includes an array of LEDs.

26. An apparatus as described in claim 25 wherein the computer causes one or more of the lights in the LED array to illuminate, and taking a sub-measurement of the bidirectional reflectance distribution function using at least in Dart the light of the one or more illuminated LEDs.

27. An apparatus as described in claim 26 wherein the one or more LEDs are lit in a sequence.

28. An apparatus for determining one or more values of a bidirectional reflectance distribution function of a subject comprising:
   a light source for producing light;
   means for taking sub-measurements of the subject with light from the light source without any physical movement between sub-measurements; and
   a computer connected to the taking means for measuring one or more values of the bidirectional reflectance distribution function of a plurality of locations of the subject simultaneously from the light sensed by the taking means.

29. An apparatus as described in claim 28 wherein the light source includes an array of LEDs.

30. An apparatus as described in claim 29 wherein the computer causes one or more of the lights in the LED array to illuminate, and taking a sub-measurement of the bidirectional reflectance distribution function using at least in part the light of the one or more illuminated LEDs.

31. An apparatus as described in claim 30 wherein the one or more LEDs are lit in a sequence.

32. An apparatus for determining one or more values of a bidirectional reflectance function of a subject comprising:
   a reflector consisting of a plurality of light reflecting surfaces;
   a sensor for sensing light from the reflector; and
   a processor connected to the sensor for determining one or more values of a bidirectional distribution function of a plurality of locations of the subject simultaneously based at least in part on light sensed by the sensor.

33. AN apparatus as described in claim 32 wherein the reflecting surfaces are slanted.

34. An apparatus as described in claim 32 including a light source which at least in part illuminates the reflector.

* * * * *